United States Patent
Bezemer et al.

(10) Patent No.: US 11,377,474 B2
(45) Date of Patent: *Jul. 5, 2022

(54) METHOD FOR PREPARING AMG 416 (ETELCALCETIDE)

(71) Applicant: AMGEN INC., Thousand Oaks, CA (US)

(72) Inventors: Jeroen Bezemer, Thousand Oaks, CA (US); Ying Chen, Newbury Park, CA (US); Richard Crockett, Thousand Oaks, CA (US); Kevin Crossley, Thousand Oaks, CA (US); Sheng Cui, Lexington, MA (US); Liang Huang, Simi Valley, CA (US); Sian Jones, Newbury Park, CA (US); Asher Lower, Moorpark, CA (US); Krishnakumar Ranganathan, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/532,344

(22) Filed: Aug. 5, 2019

(65) Prior Publication Data

US 2019/0352336 A1 Nov. 21, 2019

Related U.S. Application Data

(63) Continuation of application No. 15/300,209, filed as application No. PCT/US2015/024347 on Apr. 3, 2015.

(60) Provisional application No. 61/974,899, filed on Apr. 3, 2014.

(51) Int. Cl.
*C07K 7/06* (2006.01)
*C07K 1/107* (2006.01)
*A61K 38/00* (2006.01)

(52) U.S. Cl.
CPC .............. *C07K 7/06* (2013.01); *C07K 1/1075* (2013.01); *A61K 38/00* (2013.01)

(58) Field of Classification Search
None
See application file for complete search history.

(56) References Cited

U.S. PATENT DOCUMENTS

| | | |
|---|---|---|
| 8,378,066 B2 | 2/2013 | King et al. |
| 8,742,028 B2 | 6/2014 | Srivastava et al. |
| 2013/0079364 A1 | 3/2013 | Jenkins et al. |
| 2014/0024592 A1 | 1/2014 | Shabenpoor et al. |

FOREIGN PATENT DOCUMENTS

| | | |
|---|---|---|
| CN | 105504012 A | 4/2016 |
| CN | 107434820 A | 12/2017 |
| EP | 0339695 A2 | 11/1989 |
| JP | 2014-043468 A | 3/2014 |
| WO | WO 1998/122171 A1 | 3/1998 |
| WO | WO 2000/052040 A1 | 9/2000 |
| WO | WO 2011/014707 A2 | 2/2011 |
| WO | WO 2013/042129 A1 | 3/2013 |
| WO | WO 2014/210489 A1 | 12/2014 |
| WO | WO 2015/154031 A1 | 10/2015 |

OTHER PUBLICATIONS

Amgen, "3.2.S.2.6—Marketing Process Development, History", Excerpts from the AMGEN Manufacturing Process Development for AMG 416, pp. 2 and 14, an excerpt from the marketing authorization application (MAA) filing in Europe dated Sep. 2, 2015.
Amgen, "AMG-416 Drug Substance Stage III Process Development; Conjugation of AA1-7(SPY) with (L)-Cysteine", Excerpts from an AMGEN internal report on the development of the claimed method for preparing AMG 416, 8 pages, dated Sep. 23, 2013.
Anaspec, "Amino Acid Cartridges / FMOC-D-Amino Acid Cartridges for ABI Synthesizers", AnaSpec, Inc., Online Catalog, Copyright 2002-2016, Available on the Internet from: <URL: http://search.anaspec.com/?page=1&keywords=Fmoc&refine=y&Productcatagories+Amino+Acid+Cartridges+%F+Fmoc-D-Amin0+Acid+Cartridges+forABI+Synthesizers+%281+mmol%29, Retreived from the Internet: Dec. 15, 2016.
Andreu et al., "Chapter 7: Formation of disulfide bonds in synthetic peptides and proteins", Peptide synthesis protocols, Methods in Molecular Biology, vol. 35, pp. 91-169 (1994).
Castell et al., "The Removal of S-Cysteine Protection by Means of 2-Pyridine Sulfenyl Chloride and the Subsequent Formation of Disulfide Bonds, Preliminary communication", Helvetica Chimica Acta, vol. 62, No. 7, pp. 2507-2510 (1979).
Halocarbon, Trifluoroacetic Acid, CAS No. 76-05-1, General Data Sheet, 4 pages, Feb. 7, 2008.
Harris et al., "Studies on Deprotection of Cysteine and Selenocysteine Side-Chain Protecting Groups", J. Pept. Sci., vol. 13, No. 2, pp. 81-93 (2007).
International Search Report from PCT Patent Application No. PCT/US2015/024347 dated Sep. 1, 2015, application now published as International Publication No. WO2015/154031 on Oct. 8, 2015.
Isidro-Llobet et al., "Amino acid-protecting groups", Chem. Rev., vol. 109, No. 6, pp. 2455-2504 (2009).

(Continued)

*Primary Examiner* — Julie Ha
*Assistant Examiner* — Tara L Martinez
(74) *Attorney, Agent, or Firm* — McDermott Will & Emery LLP; Judy M. Mohr; Brennen P. Baylor

(57) ABSTRACT

A method for preparing AMG 416, or a pharmaceutically acceptable salt thereof, is provided.

14 Claims, 7 Drawing Sheets

Specification includes a Sequence Listing.

(56) References Cited

OTHER PUBLICATIONS

Matsueda et al., "Activation of conventional S-protecting groups of cysteine by conversion into the 3-nitro-2-pyridinesulfenyl (Npys) Group", Chemistry Letters, vol. 11, No. 6, pp. 921-924 (1982).
Velcalcetide, PubChem SID: 163643293, PubChem Open Chemistry Database, U.S. National Library of Medicine, National Center for Biotechnology Information, 7 pages, Available on the Internet from <URL: https://pubchem.ncbi.nlm.nih.gov/substance/163643293, Retreived from the Internet: Jun. 11, 2017.
Walter et al., "Pharmacology of AMG 416 (Velcalcetide), a novel peptide agonist of the calcium-sensing receptor, for the treatment of secondary hyperparathyroidism in hemodialysis patients", J. Pharm. Exp. Ther., vol. 346, No. 2, pp. 229-240 (2013).
Bachem AG, "Peptide User Guide, A brief introduction into synthesis methods, handling and design of peptides", Bachem Holding AG, Hauptstrasse 144, 4416 Bubendorf, Switzerland, pp. 1-21 (2009).
Baumhover et al., "Synthesis and in vitro testing of new potent polyacridine-melittin gene delivery peptides", Bioconjugate Chem., vol. 21, No. 1, pp. 74-83 (2010).
Carr, "The Handbook of Analysis and Purification of Peptides and Proteins by Reversed-Phase HPLC", Grace Vydek, Enhancing the Science of Separations, Third Edition, pp. 1-70 (2002).
Causton and Sherman, "A comparison of three- and four-helix bundle TASP molecules", J. Pept. Sci., vol. 8, No. 6, pp. 275-282 (2002).
Eidman et al., "Trifluoroacetic Acid", Encyclopedia of Reagents for Organic Synthesis, Wiley Online Library, 2 pages, Online Article accessed on Nov. 27, 2020 from: https://doi.org/10.1002/047084289X.rt236 Abstract Only.
Fletcher and Hughes, "A novel approach to the regioselective synthesis of a disulfide-linked heterodimeric bicyclic peptide mimetic of brain-derived neurotropic factor", Tetrahedron Lett., vol. 45, pp. 6999-7001 (2004).
Ghosh and Fan, "A novel method for sequence independent incorporation of activated/protected cysteine in Fmoc solid phase peptide synthesis", Tetrahedron Lett., vol. 41, pp. 165-168 (2000).
Hermansson, Bioconjugate Techniques, Third Edition, "The Reactions of Bioconjugation", and "Activation and Coupling of Affinity Ligands to Chromatography Supports", Audet, ed., pp. 242-244, and 681-685 (2013).
Hossain et al., "Regioselective disulfide solid phase synthesis chemical characterization and In Vitro receptor binding activity of equine relaxin", Int. J. Pept. Res. Ther., vol. 12, No. 3, pp. 211-215 (2006).
Hossain et al., "Synthesis, conformation, and activity of human insulin-like peptide 5 (INSL5)", ChemBioChem, vol. 9, pp. 1816-1822 (2008).
Hossain et al., "Use of a temporary "solubilizing" peptide tag for the Fmoc solid-phase synthesis of human insulin glargine via use of regioselective disulfide bond formation", Bioconjugate Chem., vol. 20, No. 7, pp. 1390-1396 (2009).
Kwak et al., "Solid phase synthesis of an analogue of insulin, A0:R glargine, that exhibits decreased mitogenic activity", Int. J. Pept. Res. Ther., vol. 16, pp. 153-158 (2010).
Li et al., "Azeotropic distillation: A review of mathematical models", Separation & Purification Reviews, vol. 34, Issue 1, pp. 87-129 (2005) Abstract Only.
Maruyama et al., "2,2'-Bispyridyl disulfide rapidly induces intramolecular disulfide bonds in peptides", Peptides, vol. 20, No. 7, pp. 881-884 (1999).
Nagata et al., "Bombyxin-II and its disulfide bond isomers: synthesis and activity", Peptides, vol. 13, No. 4, pp. 653-662 (1992).
Ruiz-Gayo et al., "Uteroglobin-like peptide cavities I. Synthesis of antiparallel and parallel dimers of bis-cysteine peptides", Tetrahedron Lett., vol. 29, No. 31, pp. 3845-3848 (1988).
Schulz et al., "Preparation of disulfide-bonded polypeptide heterodimers by titration of thio-activated peptides with thiol-containing peptides", Tetrahedron, vol. 56, pp. 3889-3891 (2000).

Ac-D-Cys(Trt)-D-Ala-D-Arg(Pbf)-D-Arg(Pbf)-D-Ala-D-Arg(Pbf)-D-Arg(Pbf)-NH-Resin

Rink Amide AM Resin

METHOD FOR PREPARING AMG 416 (ETELCALCETIDE)

CROSS-REFERENCE TO RELATED APPLICATIONS

This application is a continuation of U.S. application Ser. No. 15/300,209, filed Sep. 28, 2016, now allowed, which is a U.S. National Stage of International Patent Application No. PCT/US2015/024347, filed Apr. 3, 2015, which claims the benefit of U.S. Provisional Application No. 61/974,899, filed Apr. 3, 2014, each of which is incorporated herein by reference in its entirety.

REFERENCE TO SEQUENCE LISTING

A sequence listing is being submitted electronically via EFS in the form of a text file, created Jul. 26, 2019, and named "0419250932seqlist.txt" (2687 bytes), the contents of which are incorporated herein by reference in their entirety.

FIELD

The present disclosure relates to the field of polypeptide synthesis, and more particularly to the synthesis of AMG 416, or a pharmaceutically acceptable salt thereof.

BACKGROUND

AMG 416 is a synthetic, eight amino-acid selective peptide agonist of the calcium sensing receptor. It is being developed as an intravenous treatment of secondary hyperparathyroidism (SHPT) in hemodialysis patients with chronic kidney disease-mineral and bone disorder (CKD-MBD).

The hydrochloride salt of AMG 416 has the chemical structure:

(SEQ ID NO: 1)

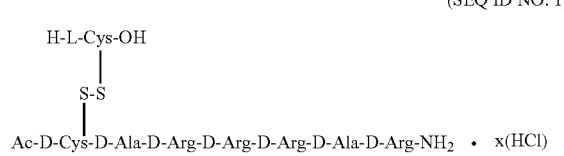

The main chain has 7 amino acids, all in the D-configuration. The side-chain cysteine residue is in the L-configuration. The molecular formula of AMG 416 (free base) is $C_{38}H_{73}N_{21}O_{10}S_2$, and has a calculated average molecular mass of 1048.3 Da.

AMG 416 and a method for its preparation are described in International Pat. Publication No. WO 2011/014707, which is incorporated herein by reference for any purpose. As described in International Pat. Publication No. WO 2011/014707, AMG 416 may be assembled by solid-phase synthesis from the corresponding Fmoc-protected D-amino acids. After cleavage from the resin, the material may be treated with Boc-L-Cys(NPyS)—OH to form the disulfide bond. The Boc group may then be removed with trifluoroacetate (TFA) and the resulting product purified by reverse-phase high pressure liquid chromatography (HPLC) and isolated as the TFA salt form by lyophilization. The TFA salt can be converted to a pharmaceutically acceptable salt by carrying out a subsequent salt exchange procedure. Such procedures are well known in the art and include, e.g., an ion exchange technique, optionally followed by purification of the resultant product (for example by reverse phase liquid chromatography or reverse osmosis).

There is a need for an efficient method of producing AMG 416, or a pharmaceutically acceptable salt thereof (e.g., AMG 416 HCl), and particularly one appropriate for commercial scale manufacturing.

SUMMARY

In view of the above-described problems, it is an objective of the disclosure to provide a method for preparing AMG 416, or a pharmaceutically acceptable salt thereof, among other things.

In a first aspect, provided is a method for preparing AMG 416, the method comprising: providing a resin-bound peptide having a structure selected from the group consisting of Fmoc-D-Cys(Trt)-D-Ala-D-Arg(Pbf)-D-Arg(Pbf)-D-Arg(Pbf)-D-Ala-D-Arg(Pbf)-[Resin] (SEQ ID NO:2) and Ac-D-Cys(Trt)-D-Ala-D-Arg(Pbf)-D-Arg(Pbf)-D-Arg(Pbf)-D-Ala-D-Arg(Pbf)-[Resin] (SEQ ID NO:3); cleaving the peptide from the solid support; and activating the side chain of the D-Cys residue of the cleaved peptide.

In one or more embodiments related to the first aspect, the cleaving and the activating steps occur in the same vessel.

In one or more further embodiments, the resin-bound peptide is contacted with a solution comprising water, trifluoroacetic acid, triisopropylsilane and dipyridyldisulfide.

In a second aspect, provided is a method for preparing AMG 416, the method comprising: providing a peptide having a structure of Ac-D-Cys(SPy)-D-Ala-D-Arg-D-Arg-D-Arg-D-Ala-D-Arg-NH$_2$ (SEQ ID NO:4); and contacting the peptide with L-Cys to produce a conjugated product.

In some embodiments related to the second aspect, the peptide is contacted with an aqueous solution comprising L-Cys and trifluoroacetic acid.

In some further embodiment related to the second aspect, the method further comprises lyophilizing the conjugated product.

In yet some further embodiments, the method of the second aspect further comprises contacting the conjugated product with an aqueous solution comprising isopropyl alcohol (IPA) and hydrochloric acid (HCl), thereby producing a precipitate comprising AMG 416 HCl.

In yet one or more further embodiments related to the second aspect, the method further comprises purifying the precipitate by high performance liquid chromatography (HPLC).

In yet a third aspect provided is a method for preparing AMG 416, the method comprising: providing a resin-bound peptide having a structure selected from the group consisting of Fmoc-D-Cys(Trt)-D-Ala-D-Arg(Pbf)-D-Arg(Pbf)-D-Arg(Pbf)-D-Ala-D-Arg(Pbf)-[Resin] (SEQ ID NO:2) and Ac-D-Cys(Trt)-D-Ala-D-Arg(Pbf)-D-Arg(Pbf)-D-Arg(Pbf)-D-Ala-D-Arg(Pbf)-[Resin] (SEQ ID NO:3); cleaving the peptide from the solid support, i.e., to provide an unsupported peptide, and activating the side chain of the D-Cys residue of the unsupported peptide to generate an AMG 416 SPy intermediate (where SPy is 2-pyridinesulfenyl or S-Pyr), dissolving the AMG 416 SPy intermediate in an aqueous 0.1% TFA (trifluoroacetic acid solution), and purifying the AMG 416 SPy derivative by HPLC.

In some embodiments related to the third aspect, the method further comprises azeotropic distillation of the AMG 416 SPy intermediate, to thereby effect a solvent exchange to produce a solution of the AMG 416 SPy in the new solvent, e.g., water and isopropyl alcohol.

In yet some additional embodiments related to the third aspect, the method further comprises contacting the isopropyl alcohol-water solution of the AMG 416 SPy, in some embodiments in the form of its trifluoroacetate salt, with an aqueous solution comprising L-Cys.

In a fourth aspect, provided is a method for preparing H-D-Arg(Pbf)-OH, i.e., a suitable starting material for certain of the synthetic methods provided herein.

In some embodiments related to the fourth aspect, the method comprises converting Boc-D-Arg-OH to Boc-D-Arg(Pbf)-OH in the presence of NaI (sodium iodide). In yet some further embodiments, the sodium iodide is present at a concentration of about 5% mol.

In some additional embodiments related to the fourth aspect, the method further comprises converting Boc-D-Arg(Pbf)-OH to D-Arg(Pbf)-OH, and crystallizing the D-Arg(Pbf)-OH in an IPA/water solvent system.

Additional embodiments of the methods described herein will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention.

DETAILED DESCRIPTION

Figure 1:
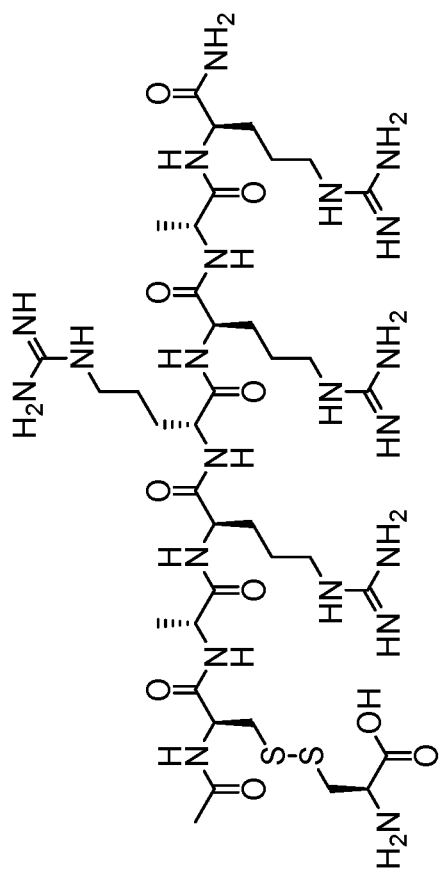
FIG. 1 shows the chemical structure of AMG 416 (Ac-D-Cys(L-Cys-OH)-D-Ala-D-Arg-D-Arg-D-Arg-D-Ala-D-Arg-NH$_2$) (SEQ ID NO:1).

The present disclosure now will be described more fully hereinafter. This disclosure may, however, be embodied in many different forms and should not be construed as limited to the embodiments set forth herein; rather, these embodiments are provided so that this disclosure will be thorough and complete, and will fully convey its scope to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, peptide, chemistry, etc., portions pertaining to such compounds, chemistry, etc. are those portions of the document which are incorporated herein by reference.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, molecular biology and protein chemistry described herein are those well-known and commonly used in the art. The methods and techniques of the present application are generally performed according to conventional methods well known in the art and as described in various general and more specific references that are cited and discussed throughout the present specification unless otherwise indicated. See, e.g., Laszlo, *Peptide-Based Drug Design: Methods and Protocols*, Humana Press (2008); Benoiton, *Chemistry of Peptide Synthesis*, CRC Press (2005); Ausubel et al., *Current Protocols in Molecular Biology*, Greene Publishing Associates (1992), which are incorporated herein by reference for any purpose. Purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this disclosure is not limited to the particular methodology, protocols, and reagents, etc., described herein and as such may vary. The terminology used herein is for the purpose of describing particular embodiments only, and is not intended to limit the scope of the disclosed, which is defined solely by the claims.

The term "about," particularly in reference to a given quantity, is meant to encompass deviations of plus or minus five percent.

I. General Definitions

The articles "a" and "an" are used herein to refer to one or to more than one (i.e., to at least one) of the grammatical object of the article, unless specifically indicated otherwise. By way of example, "an element" means one element or more than one element.

The term "AMG 416", also known as etelcalcetide, formerly known as velcalcetide or KAI-4169, refers to a compound having the chemical name: N-acetyl-D-cysteinyl-D-alanyl-D-arginyl-D-arginyl-D-arginyl-D-alanyl-D-arginamide disulfide with L-cysteine, which has the following structural formula:

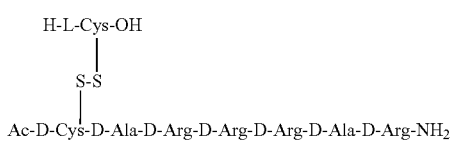

Reference to AMG 416, or to any compound or AMG 416 fragment, intermediate, or precursor as described herein, is intended to encompass neutral, uncharged forms thereof, as well as pharmaceutically acceptable salts, hydrates and solvates thereof.

The terms "AMG 416 hydrochloride" and "AMG 416 HCl" are interchangeable and refer to a hydrochloride salt form of AMG 416 having the following structural formula:

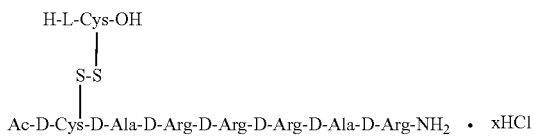

Generally, x has a value of 3-5 (e.g., 3, 4 or 5).

"Pharmaceutically acceptable salt" refers to a salt form of a compound having at least one group suitable for salt formation that causes no significant adverse toxicological effects to a patient. The term "pharmaceutically-acceptable salt" may, in one respect, refer to the relatively non-toxic, inorganic or organic acid addition salts of compounds as provided herein, e.g., AMG 416, as well as AMG 416 fragments, intermediates, precursors, and the like, possessing one or more ionizable amine groups. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19). Additional suitable pharmaceutically acceptable salt forms can be found in, e.g., Handbook of Pharmaceutical Salts: Properties, Selection and Use, Weinheim/Zürich:Wiley-VCH/VHCA, 2002; P. H. Stahl and C. G. Wermuth, Eds.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids. A "free amino acid" or "free amino group" refers to an amino acid, peptide fragment, or peptide having an amino group that is in the form of —$NH_2$, that is, is unprotected.

The phrase "protecting group" or "PG" as used herein refers to a temporary substituent or substituents that protect a potentially reactive functional group from an undesired chemical transformation. Examples of such protecting groups include esters of carboxylic acids, silyl ethers of alcohols, and acetals and ketals of aldehydes and ketones, respectively. See, e.g., Greene, T. W.; Wuts, P. G. M. Protective Groups in Organic Synthesis, 4th ed.; Wiley: New York, 2007; Isidro-Llobet, A., et al., Amino Acid-Protecting Groups, Chem. Rev 2009, 109, 2455-2504. Reactive amino acids or peptide fragments as described herein often suitably contain one or more protecting groups on functionalities that are not the target of a subject chemical transformation. Exemplary protecting groups include, e.g., carboxybenzyl, also referred to as benzyloxycarbonyl ("Cbz" or "Z"), 9-fluuorenylmethoxycarbonyl (Fmoc), 2,2,4,6,7-pentamethyldihydrobenzofuran-5-sulfonyl (Phf), tert-butyloxycarbonyl (Boc), trityl (Trt), methyl ester (OMe), 2-pyridinesulfenyl (SPy or S-Pyr), amide, and the like. In the shorthand structures provided herein, —$NH_2$ at the C-terminus signifies an amide protecting group (—$C(O)NH_2$), "H" at the N-terminus refers to a free amino group, and designation of a protecting group in parentheses signifies that the protecting group is on the δ nitrogen of ornithine.

As used herein, the term "protection eliminating agent" or "deprotecting agent" can be used interchangeably, and is a chemical reagent for removing amino-protecting agents connected on amino acids, and the amino-protecting agent can be well-known in the field, such as, but not limited to Fmoc and Boc.

As used herein, the terms "coupling agent", "condensing agent", "activating agent," "condensation activating agent," used interchangeably herein, refer to a chemical reagent that facilitates reaction of an amino group from one amino acid with a carboxyl group from another amino acid to form a peptide bond. Exemplary coupling agents are well-known in the art and include but are not limited to carbodiimides such as N,N'-diisopropylcarbodiimide (DIC), dicyclohexylcarbodiimide (DCC), 1-[Bis(dimethylamino)methylene]-1H-1,2,3-triazolo[4,5-b] pyridinium 3-oxide hexafluorophosphate (HATU), [benzotriazol-1-yloxy(dimethylamino)methylidene]-dimethylazanium; tetrafluoroborate (TBTU), N,N,N', N'-tetramethyl-O-(1H-benzotriazol-1-yl)uronium hexafluorophosphate, O-(benzotriazol-1-yl)-N,N,N',N'-tetramethyluronium hexafluorophosphate (HBTU), and N,N-diisopropyletyl amine (DIPEA). See, e.g., El-Faham, A. and Albericio, F., "Peptide Coupling Reagents, More than a Letter Soup", Chem. Rev. 2011, 111, 6557-6602. Such compounds are readily available from commercial vendors.

As used herein, the term "cleavage agent" refers to a chemical agent which can separate a peptide bound to a resin from the resin. Cleavage agents are well-known to those of ordinary skill in the art and include a acid solution comprising TFA and HCl solution.

The term "treating" refers to any indicia of success in the treatment or amelioration of an injury, pathology or condition, including any objective or subjective parameter such as abatement; remission; diminishing of signs or symptoms or making the injury, pathology or condition more tolerable to the patient; slowing in the rate of degeneration or decline; making the final point of degeneration less debilitating; improving a patient's physical or mental well-being. The treatment or amelioration of signs or symptoms can be based on objective or subjective parameters; including the results of a physical examination. For example, certain methods presented herein successfully treat SHPT in hemodialysis patients with CKD-MBD by decreasing serum intact parathyroid hormone (iPTH).

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with the disease state (e.g., elevated PTH levels). A "therapeutically effective amount" is an amount sufficient to remedy a disease state or symptoms, particularly a state or symptoms associated with the disease state, or otherwise prevent, hinder, retard or reverse the progression of the disease state or any other undesirable symptom associated with the disease in any way whatsoever. The full therapeutic effect does not necessarily occur by administration of one dose, and may occur only after administration of a series of doses. Thus, a therapeutically effective amount may be administered in one or more administrations.

The terms "therapeutically effective dose" and "therapeutically effective amount," as used herein, means an amount that elicits a biological or medicinal response in a tissue system, animal, or human being sought by a researcher, physician, or other clinician, which includes alleviation or amelioration of the signs or symptoms of the disease or disorder being treated, i.e., an amount of velcalcetide that supports an observable level of one or more desired biological or medicinal response, for example lowering iPTH.

The terms "peptide," "polypeptide" and "protein" are interchangeable and refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Peptides, polypeptides and proteins can be produced by a liquid-phase synthesis or solid phase synthesis or by a genetically-engineered or recombinant cell, and comprise molecules having the amino acid sequence.

A "variant" of a peptide or polypeptide comprises an amino acid sequence wherein one or more amino acid residues are inserted into, deleted from and/or substituted into the amino acid sequence relative to another polypeptide sequence. Variants include fusion proteins.

A "derivative" of a peptide or polypeptide is a peptide or polypeptide that has been chemically modified in some manner distinct from insertion, deletion, or substitution variants, e.g., via conjugation to another chemical moiety. Such modification can include the covalent addition of a group to the amino and/or carboxy termini of the peptide or polypeptide, e.g., acetylation of the amino terminus and/or amidation of the carboxy terminus of a peptide or polypeptide.

The term "amino acid" includes its normal meaning in the art. The twenty naturally-occurring amino acids and their abbreviations follow conventional usage. See, Immunology—A Synthesis, 2nd Edition, (E. S. Golub and D. R. Green, eds.), Sinauer Associates: Sunderland, Mass. (1991), which is incorporated herein by reference for any purpose. Stereoisomers (e.g., D-amino acids) of the 19 conventional amino acids (except glycine), unnatural amino acids such as [alpha]-, [alpha]-disubstituted amino acids, N-alkyl amino acids, and other unconventional amino acids may also be suitable components for polypeptides and are included in the phrase "amino acid." Examples of unconventional amino acids include: homocysteine, ornithine, 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A "subject" or "patient" as used herein can be any mammal. In a typical embodiment, the subject or patient is a human.

The term "q.s." means adding a quantity sufficient to achieve a desired function, e.g., to bring a solution to the desired volume (i.e., 100%).

II. Embodiments

In one or more embodiments, AMG 416 hydrochloride is prepared via a series of process stages as follows: exemplary stages include the solid phase peptide synthesis of a seven-member linear fragment (stage I) of AMG 416, followed by cleavage of the peptide chain from the resin with concomitant side chain deprotection and cysteine activation (stage II), followed by in-situ conjugation of the peptide chain with L-Cys (disulfide formation) to provide crude AMG 416 (stage III), followed, in some embodiments, immediately, by preparative HPLC and lyophilization to provide purified AMG 416 TFA salt (stage IV). Stage IV is followed by a subsequent salt exchange (TFA to HCl) by precipitation, and in some embodiments, followed by microfiltration and lyophilization to provide the purified AMG 416 hydrochloride salt (stage V).

Solid Phase Peptide Synthesis

The seven-membered linear fragment of AMG 416 may be synthesized by any method known in the art, including solid phase peptide synthesis (SPPS). As used herein, the term "solid phase synthesis" or "solid phase peptide synthesis" refers to a method, well-known to one of ordinary skill in the art, in which a growing peptide chain is linked to a solid support. Solid phase synthesis typically comprises the steps of: (i) covalently binding a first amino acid (whose amino-group is blocked or "protected") to a solid phase carrier; (ii) removing the protecting group from the amino-group using a deprotecting agent; (iii) activating the carboxyl of a second amino acid (whose amino-group is blocked) and contacting the second amino acid with the first amino acid bound to the solid phase carrier so that a dipeptide (whose amino-group is blocked) is obtained; (iv) repeating the peptide bond formation steps and thus the peptide chain is extended from C-terminal to N-terminal; and (v) removing the protecting group of the amino-group and separating the peptide chain from the solid phase carrier with a cleavage agent to yield a peptide.

Suitable techniques of solid phase synthesis are well known in the art, and include those described in Merrifield, in *Chem. Polypeptides*, pp. 335-61 (Katsoyannis and Panayotis eds. 1973); Merrifield, *J. Am. Chem. Soc.* 85:2149 (1963); Davis et al., *Biochem. Intl.* 10:394-414 (1985); Stewart and Young, *Solid Phase Peptide Synthesis* (1969); U.S. Pat. No. 3,941,763; Finn et al., *The Proteins*, 3rd ed., vol. 2, pp. 105-253 (1976); and Erickson et al., The Proteins, 3rd ed., vol. 2, pp. 257-527 (1976). See, also Houben-Weyl, *Methods of Organic Chemistry*. Additional Supplementary Volumes to the $4^{th}$ Ed., Vol E22A, "*Synthesis of Peptides and Peptidomimetics*", Editor-in-Chief M. Goodman. Georg Thieme Verlag: Stuttgard and New York. 2002, pp. 685-877; Chan, W. C., White, P. D., "*Fmoc Solid Phase Peptide Synthesis, A Practical Approach*". Oxford University Press, (200), p. 9-109. Solid phase synthesis is typically a preferred technique of making individual peptides such as AMG 416, since it is often one of the most cost-effective methods of making small peptides.

In some embodiments, the main chain linear fragment of AMG 416 is assembled using standard solid-phase peptide synthesis protocols employing Fmoc-protection strategy and, for example, a Rink amide (RAM) resin such as available from Sigma Aldrich, to provide the C-terminus resin-bonded amide, along with acetylation of the peptide N-terminus. In some other embodiments, other resins and linkers may be used (e.g., Ramage amide AM resin, also referred as tricyclic amide linker resin). In one embodiment, assembly of the main chain linear fragment comprises the steps of: (i) mixing an Fmoc-Rink amide AM resin with a deprotecting agent to obtain a Rink amide AM resin; (ii) condensing Fmoc-D-Arg(Pbf)-OH with the Rink amide AM resin to obtain an Fmoc-D-Arg(Pbf)-Rink amide AM resin; (iii) repeating the Fmoc deprotection in step (i) and the condensation between an amino acid and a polypeptide on the resin in step (ii) for each remaining amino acid residue of the main chain linear fragment of AMG 416, proceeding from the C-terminal to the N-terminal (e.g., using Fmoc-D-Cys(Trt)-OH, Fmoc-D-Ala-OH and Fmoc-D-Arg(Pbf)-OH) to form a polypeptide resin represented by SEQ ID NO:2; and (iv) repeating the Fmoc deprotection in step (i) and acetylating the N-terminus to form a polypeptide resin represented by SEQ ID NO:3. See FIG. 2.

(SEQ ID NO: 2)
Fmoc-D-Cys(Trt)-D-Ala-D-Arg(Pbf)-D-Arg(Pbf)-D-

Arg(Pbf)-D-Ala-D-Arg(Pbf)-[Resin]

(SEQ ID NO: 3)
Ac-D-Cys(Trt)-D-Ala-D-Arg(Pbf)-D-Arg(Pbf)-D-

Arg(Pbf)-D-Ala-D-Arg(Pbf)-[Resin]

Typically, cleavage of the Fmoc protecting group is achieved using a deprotecting agent such as piperidine in DMF. In one embodiment, coupling of the Fmoc-protected amino acid is carried out in a solvent such as dimethylformamide (DMF) using a suitable coupling agent such as the carbodiimide coupling agent, N,N-diisopropylcarbodiimide (DIC), optionally in the presence of an additive such as ethyl 2-cyano-2-(hydroxyimino) acetate (Oxyma) for all amino acids except cysteine. In the case of peptide chain elongation with cysteine, coupling is typically carried out using N,N-diisopropylcarbodiimide (DIC) in the presence of a benzotriazole additive such as hydroxybenzotriazole (HOBT) in a solvent system such as dimethyl formamide-dichloromethane, (i.e., DMF, DCM, HOBt, DIC).

Acetylation of the N-terminus may be accomplished by any method known in the art. In one embodiment, acetylation of the N-terminus is carried out using, for example, acetic anhydride ($Ac_2O$) in pyridine and DMF.

Cleavage from Resin

The peptide may be separated from the support, and the protecting groups may be removed from the side chains by any means known in the art. See, e.g., *Synthetic Peptides: A User's Guide* (G. A. Grant, ed.), W. H. Freeman and Company, New York, 1992; and Chan, W. C., White, P. D. "Fmoc Solid Phase Peptide Synthesis, A Practical Approach", Oxford University Press (2000), p. 64-66 and 105-109.

Figure 3:
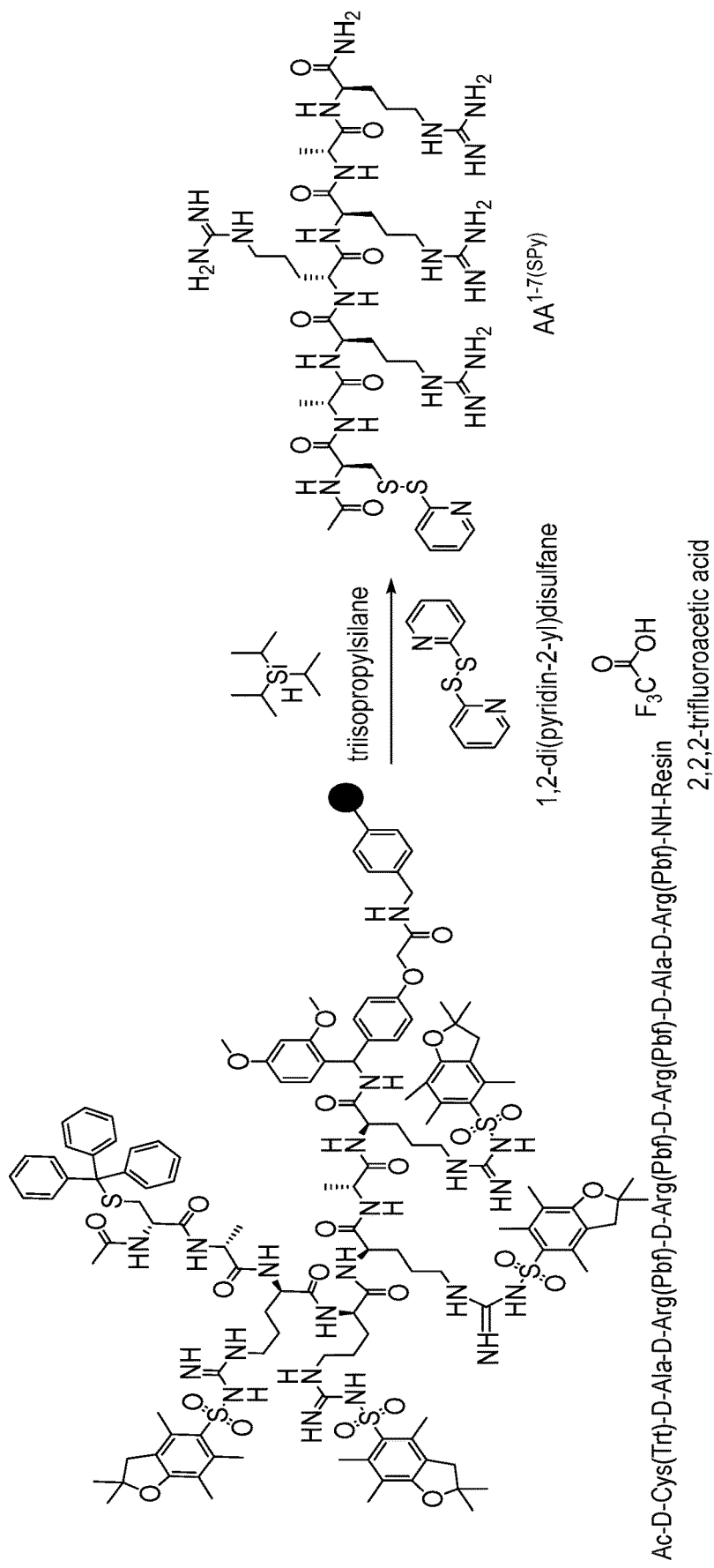
FIG. 3 shows a reaction scheme in which the SPy intermediate product (Ac-D-Cys(SPy)-D-Ala-D-Arg-D-Arg-D-Arg-D-Ala-D-Arg-NH$_2$) (SEQ ID NO:4) is formed from the peptidyl-resin (Ac-D-Cys(Trt)-D-Ala-D-Arg(Pbf)-D-Arg(Pbf)-D-Arg(Pbf)-D-Ala-D-Arg(Pbf)-NH-Resin) (SEQ ID NO:3).

In one embodiment, the peptidyl-resin is added to a cocktail solution comprising water (e.g., deionized water (DIW)) trifluoroacetic acid (TFA), triisopropylsilane (TIPS) and dipyridyldisulfide (DPDS). This allows the peptide to be separated from the resin with concomitant side-chain deprotection and cysteine activation, thus preparing for the in-situ conjugating to L-Cys. The seven-amino acid SPy intermediate product ($AA^{1-7(SPy)}$) is produced. See FIG. 3. The sequence of the SPy intermediate product is provided in SEQ ID NO:4.

(SEQ ID NO: 4)
Ac-D-Cys(SPy)-D-Ala-D-Arg-D-Arg-D-Arg-D-Ala-D-Arg- $NH_2$

In-Situ Conjugation and Preparative HPLC

The SPy intermediate product may be conjugated to L-Cys by any method known in the art. In one embodiment, conjugation of L-Cys is performed in aqueous TFA.

Figure 4:
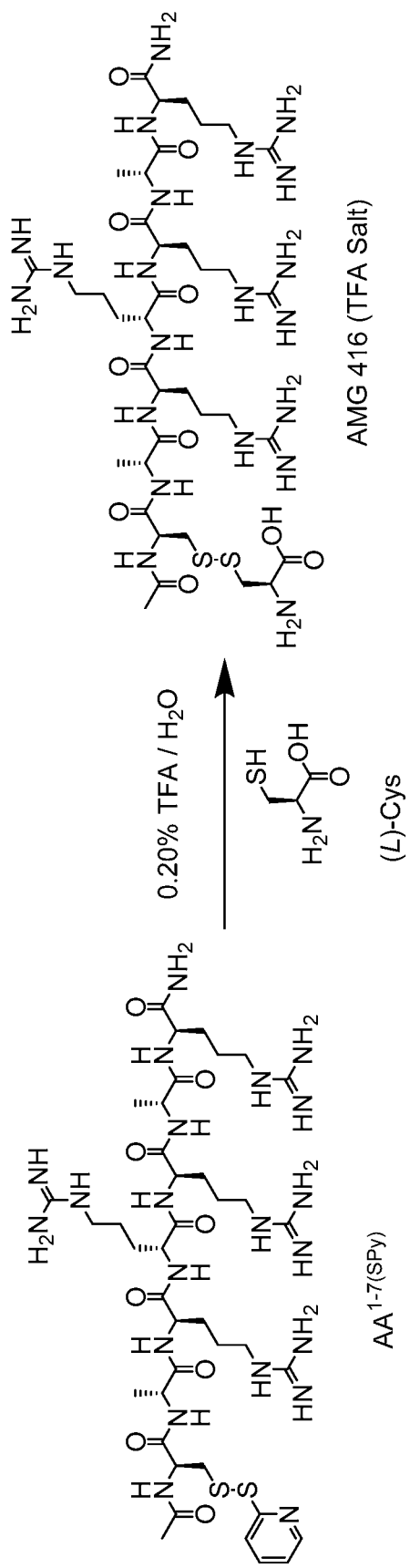
FIG. 4 shows a reaction scheme in which a TFA salt of AMG 416 is formed from the SPy intermediate ($AA^{1-7(SPy)}$).

The AMG 416 (TFA salt) produced may be purified by any means known in the art. In one embodiment, AMG 416 (TFA salt) is purified by high pressure liquid chromatography (HPLC). For example, in one embodiment, the purification and concentration of the AMG 416 (TFA salt) comprises a reverse-phase HPLC purification step and a reverse-phase HPLC concentration step. See FIG. 4.

The purified and concentrated sample containing AMG 416 (TFA salt) may be lyophilized.

Salt Conversion

The TFA salt may be converted to pharmaceutically acceptable salt, such as the hydrochloride salt, by any means known in the art.

Figure 5:
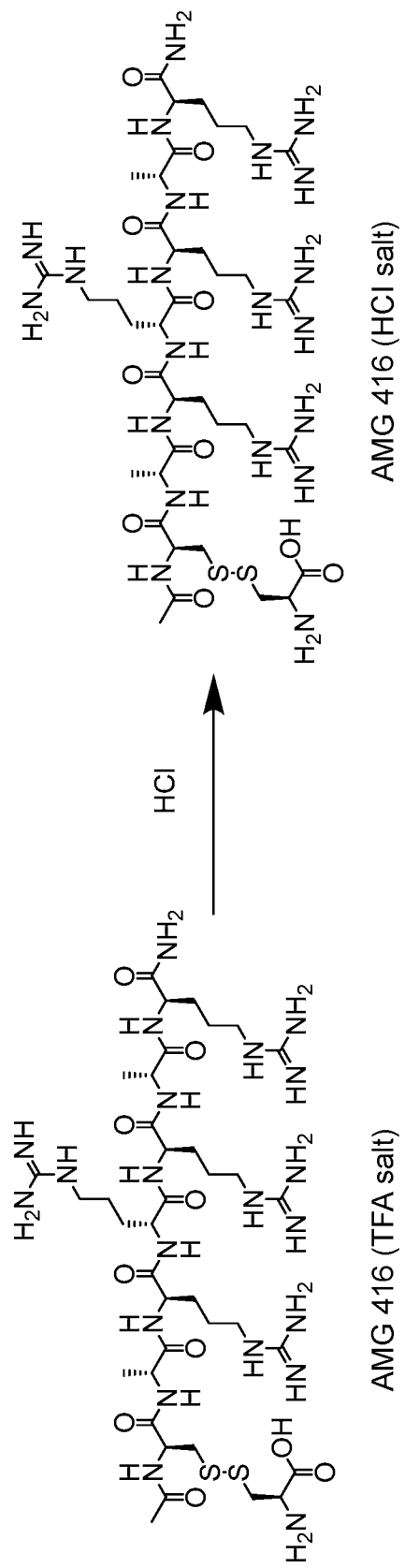
FIG. 5 shows a reaction scheme in which the HCl salt of AMG 416 is formed from the TFA salt of AMG 416.

In one embodiment, the lyophilized TFA salt of AMG 416 is dissolved in an aqueous solution of isopropyl alcohol (IPA). The TFA salt solution is then charged to an HCl solution for salt exchange and precipitation of the HCl salt. The precipitate may then be reconstituted with water, filtered thought a micro-filter (e.g., 0.2 µm filter) and lyophilized to isolate the HCl salt of AMG 416. See FIG. 5.

Purification of a SPy Intermediate

In an alternative embodiment, the SPy intermediate product is purified prior to conjugation to the L-Cys. Generally, SPy intermediate products, in particular peptide-SPy intermediates, are considered to be highly unstable, i.e., are thought to not be sufficiently stable to withstand efficient purification, such as by HPLC. However, in arriving at the methods provided herein, it was discovered by the Applicants that, unexpectedly, the peptide-SPy intermediates prepared according to the methods described herein are indeed sufficiently stable to withstand a separate purification step. Moreover, it was further discovered that purification of such intermediates prior to conjugation to the L-Cys can actually increase the efficiency and decrease the cost of manufacture of the final peptide drug product.

In an exemplary embodiment, the alternative method is carried out as follows. The method described below and in Example 5 is useful for the purification of a SPy intermediate as provided herein, wherein the intermediate remains stable and is suitable for conjugation to a thiol-containing moiety, e.g., via disulfide bond formation. For example, the peptide-SPy intermediate is dissolved in an aqueous solution containing no more than about 0.2% TFA, for example, about 0.05% to 0.15% TFA, or about 0.1% TFA, and is then directly applied to an HPLC column for chromatographic purification. Solvent exchange of the HPLC fractions containing the peptide-SPy intermediate can then be carried out, for example, by azeotropic distillation. Following solvent exchange of the peptide-SPy intermediate into an appropriate solvent, such as a mixture of water-isopropanol, a thiol-containing moiety, such as L-Cys is added directly to the peptide-SPy intermediate solution to effect conjugation. The resultant conjugated product, e.g., in solution, is then available for salt exchange.

A particular embodiment of the foregoing purification method is as follows. After the initial cleavage of the peptide from the resin support and isolation of the $AA^{1-7(SPy)}$ intermediate product, the intermediate is dissolved in 0.1% TFA and acetonitrile, loaded onto a stationary phase HPLC column and purified as described above. The use of a 0.1% TFA solution has multiple advantages for HPLC purification when compared to the use of, for example, a 0.2% TFA solution. For instance, 0.1% TFA is less damaging to the stationary phase during the purification process than a higher concentration TFA solution. That is to say, by using such an optimized concentration of TFA, there is less decomposition of the stationary phase, thereby resulting in a longer lifetime for the stationary phase. Moreover, the peptide-SPy intermediate (e.g., $AA^{1-7(SPy)}$) product is less polar, resulting in the intermediate being better retained on the reverse phase stationary phase. As a result, much higher loading onto the stationary phase can be achieved in each purification run. In some embodiments, the increased loading capacity increases the throughput of the manufacturing process 1.5 to 2-fold, or about 1.5-fold.

The HPLC fractions containing the SPy intermediate product as a TFA salt are then subjected to azeotropic distillation with sufficient IPA charges to change the solvent from the acetonitrile and water to a 15% water in IPA solution suitable for L-Cys conjugation and salt exchange. This method is particularly advantageous as both the conjugation and salt exchange can be carried out in a single vessel, further improving the efficiency and feasibility of the manufacturing process.

Manufacture of Fmoc-D-Arg(Pbf)-OH Starting Material

AMG 416 comprises a linear sequence of 7 amino acids, 4 of which are D-arginines. Disclosed herein is a method for synthesizing Fmoc-D-Arg(Pbf)-OH, the Fmoc derivative of D-arginine used in the synthesis of AMG 416. Use of a high quality Fmoc-D-Arg(Pbf)-OH starting material can furnish additional purity to crude AMG 416 from stage I to stage III, to thereby enhance the purification yield in stage IV. More importantly, the use of a high quality, high purity starting material can provide a desirable and advantageous control element to secure the desired purity of AMG 416. A new process for preparing high quality D-Arg(Pbf)-OH and Fmoc-D-Arg(Pbf)-OH has been developed which produces a higher yield, requires fewer unit operations, provides more robust quality control and is amenable to large scale manufacturing. In summary, the method of preparing Fmoc-D-Arg(Pbf)-OH described herein represents a significant increase in the feasibility of AMG 416 manufacturing accompanied by a potential gain in quality.

A synthetic route that is one of the most concise syntheses of Fmoc-D-Arg(Pbf)-OH found in the literature and which can be used for the commercial scale synthesis of Fmoc-D-Arg(Pbf)-OH is as follows. See, e.g., Chinese Patent No. CN101250172B, 2 May 2012. The synthesis starts by protecting the amino group of D-Arg with di-tert-butyl dicarbonate ($Boc_2O$) yielding Boc-D-Arg-OH in an approximately quantitative yield after the isolation. In step 2, the side chain guanidine group is protected with a Pbf group in the presence of a base such as aqueous sodium hydroxide. The product is used directly in the next step as an IPA (isopropyl alcohol) solution without isolation. Step 3 comprises removing the Boc protecting group under acidic conditions, and isolating the corresponding product, D-Arg(Pbf)-OH, as a crystalline intermediate. Step 4 of the process comprises installing an Fmoc protecting group on the amino functionality to afford Fmoc-D-Arg(Pbf)-OH as the final product. Since both step 2 and step 4 products are amorphous materials, i.e., providing limited capability to reject impurities, the crystalline intermediate D-Arg(Pbf)-OH (step 3 product) serves as a control point to influence and secure the purity of the final product.

To obtain a high purity product is a significant challenge when relying on processes reported in the literature. Multiple recrystallizations are typically required to meet the purity requirement. As an example, D-Arg(Pbf)-OH is recrystallized seven times in an EtOH/EtOAc/water tertiary solvent system in order to upgrade the purity to a desired level. In addition, in step 2, 20-30% of the starting materials remain unreacted even in the presence of a large excess of sodium hydroxide and PbfCl, and the overall yield (step 1 to 3) is typically only less than 40%.

Figure 6:
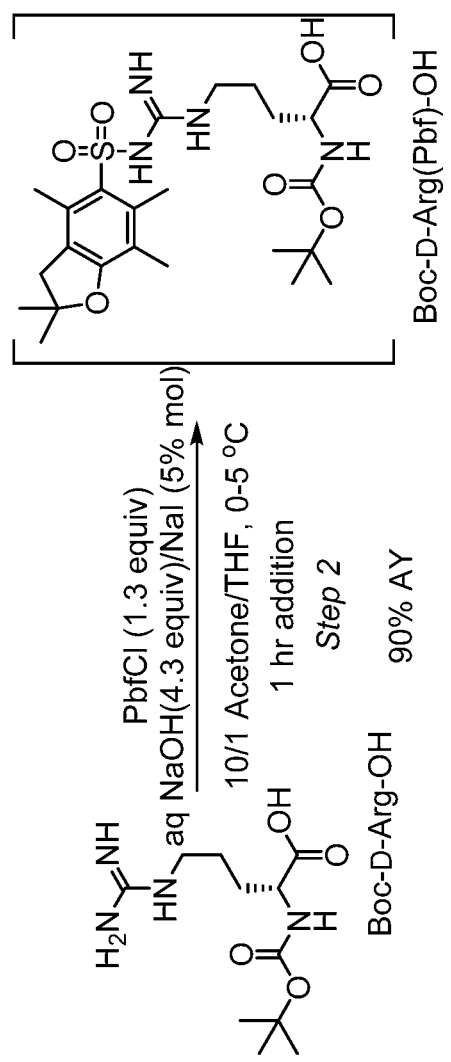
FIG. 6 shows a reaction scheme in which Boc-D-Arg(Pbf)-OH is formed from Boc-D-Arg-OH.
Figure 7:
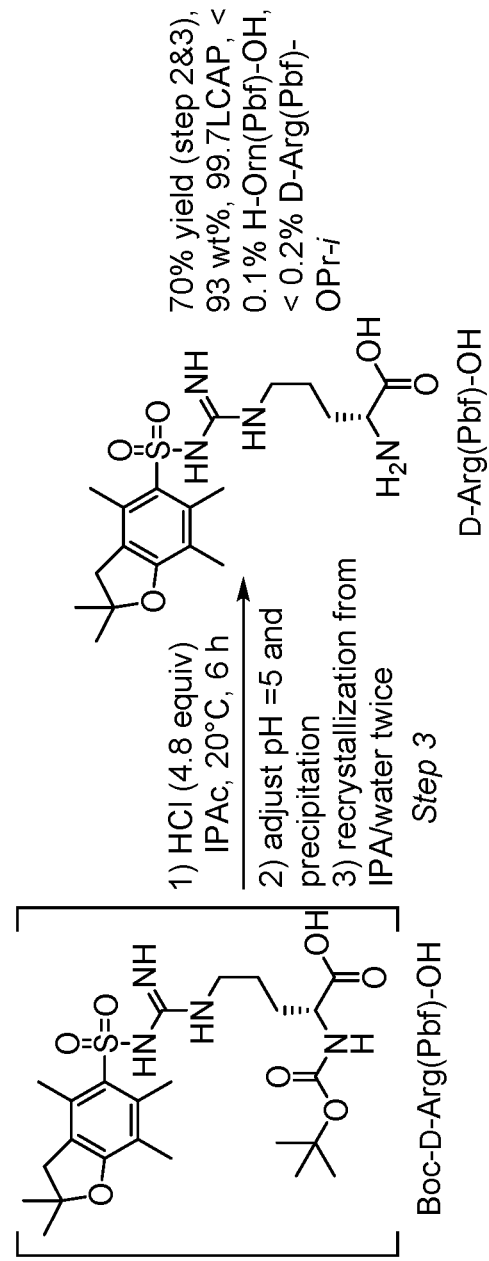
FIG. 7 shows a reaction scheme in which D-Arg(Pbf)-OH is formed from Boc-D-Arg(Pbf)-OH.

The improved process developed and described herein and illustrated in FIGS. 6 and 7, provides several advantages over known processes. NaI is introduced as a catalyst for converting Boc-D-Arg-OH to Boc-D-Arg(Pbf)-OH (see Step 2 in FIG. 6). The incorporation of sodium iodide is effective to significantly improve the reaction kinetics and as a result, the conversion of step 2 can be increased to greater than 95%, and the assay yield can be improved up to ~90%. In addition, the total quantity of impurities is also reduced.

D-Orn(Pbf)-OH and the ethyl ester of D-Arg(Pbf)-OH are key impurities formed in step 2 and step 3 (FIG. 7), respectively, and are difficult to remove via crystallization, thereby contributing to the need for multiple recrystallizations. The improved process described herein further comprises the use of isopropyl acetate (IPAc), a more sterically hindered ester when compared to the more commonly used EtOAc, as the solvent for step 3 in which Boc-D-Arg(Pbf)-OH is converted to D-Arg(Pbf)-OH. The use of IPAc significantly slows down the side reaction, transesterification, catalyzed by the strong acid, HCl. As a result, the content of corresponding impurity, the ester of D-Arg(Pbf)-OH, is reduced to less than about 0.5% (vs greater than 1.0% in the process which employs EtOAc). Additionally, isopropyl alcohol (IPA)/water was found to be a more powerful solvent system which allowed removal of all process impurities yet minimized product loss in the crystallization steps. In a test run conducted at a laboratory scale (20 g), the purity of D-Arg(Pbf)-OH (step 3 intermediate) was improved to greater than 99.7% with only two crystallizations, and the overall yield (step 1 to 3) was approximately 70%. One embodiment of this improved process is described in Example 6 below.

The skilled artisan will readily appreciate that the present disclosure also extends to variants and derivatives of AMG 416. For example, in one embodiment, the methods provided herein may also be used with N-acetyl-D-cysteinyl-D-alanyl-D-arginyl-D-arginyl-D-arginyl-D-alanyl-D-arginamide disulfide with D-cysteine. In another embodiment, the disclosed formulations also may be used with N-acetyl-L-cysteinyl-L-alanyl-L-arginyl-L-arginyl-L-arginyl-L-alanyl-L-arginamide disulfide with D-cysteine and/or N-acetyl-L-cysteinyl-L-alanyl-L-arginyl-L-arginyl-L-arginyl-L-alanyl-L-arginamide disulfide with L-cysteine. In another embodiment, the disclosed formulation may also be used with N-acetyl-D-cysteinyl-D-arginyl-D-alanyl-D-arginyl-D-arginyl-D-alanyl-D-arginamide disulfide with L-cysteine, and/or N-acetyl-D-cysteinyl-D-arginyl-D-alanyl-D-arginyl-D-arginyl-D-alanyl-D-arginamide disulfide with D-cysteine. Additionally, the instant methods may be employed to prepare one or more of the compounds provided in Table 1, Table 2, Table 3, Table 4, Table 5, Table 6, Table 7, Table 8, Table 9 and/or Table 10 of International Pat. Publication No. WO 2011/014707. In further embodiments, the methods described herein may also be used to prepare compounds described in International Pat. Publication No. WO 2011/014707.

EXAMPLES

The following examples, including the experiments conducted and the results achieved, are provided for illustrative purposes only and are not to be construed as limiting the scope of the appended claims.

Example 1A

Synthesis of the Main Chain Linear Fragment

Figure 2:
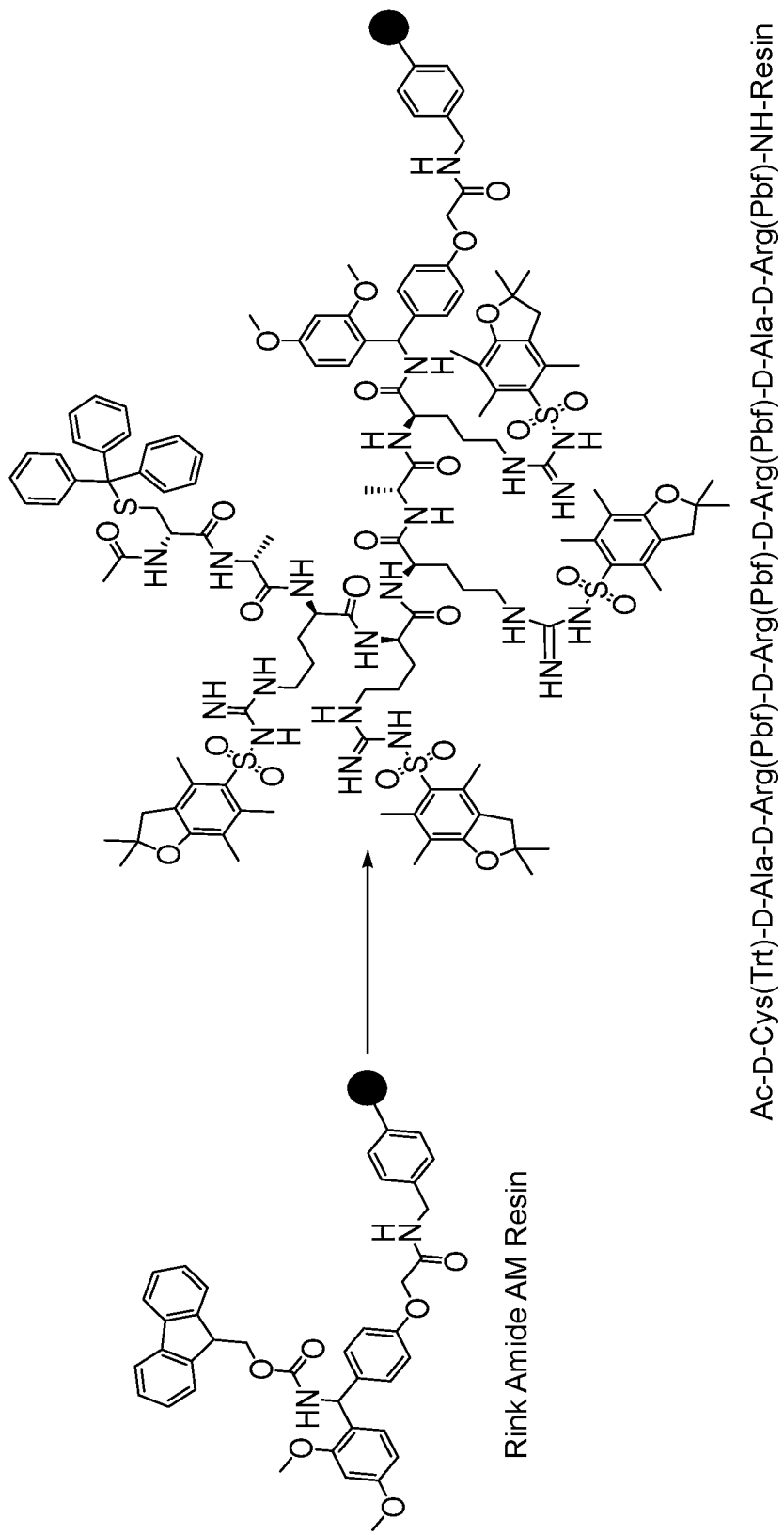
FIG. 2 shows the chemical structure of Rink Amide AM resin and Ac-D-Cys(Trt)-D-Ala-D-Arg(Pbf)-D-Arg(Pbf)-D-Arg(Pbf)-D-Ala-D-Arg(Pbf)-Resin (SEQ ID NO:3).

Synthesis of the main chain linear fragment is shown in FIG. 2. Rink Amide AM Resin (Fmoc 2,4-dimethoxy-4' (carboxymethyloxy)-benzhydrylamine linked to Aminomethyl Resin) (1 kg) was added to DMF (5.8 L/kg) and the solution was agitated at 22° C. The resin was filtered and slurry washed. A sample was tested for residual Fmoc (UV test) and residual piperidine (pH). The Kaiser and/or TNBS color tests were conducted to ensure that Fmoc deprotection had been carried out.

The first six amino acid derivative couplings followed the same procedure for pre-activation, coupling and washing. 1.6 eq of the protected Fmoc amino acid was added to DMF, 8.9 L/kg at 22° C. Oxyma (2.45 eq) was then added. The solution was cooled to 21° C. and DIC (2.13 eq) was added, and the reaction was allowed to proceed. The pre-activated solution was combined with resin and the reaction was allowed to proceed. DIC (1.07 eq) was added and the reaction was allowed to proceed at 22° C. A sample was tested for incomplete coupling using the Kaiser and/or TNBS color tests. The material was washed, followed by Fmoc deprotection and further washing. A sample was tested for residual Fmoc (UV test) and residual piperidine (pH). The Kaiser and/or TNBS color tests were conducted to ensure Fmoc deprotection had taken place.

Fmoc-D-Cys(Trt)-OH 1.6 eq was added to a 1:1.7 DMF: DCM solution, 12 L/kg, followed by addition of HOBt.H$_2$O (2.45 eq). The solution was cooled to 20° C. and DIC (2.13 eq) was added and the reaction was allowed to proceed. The Pre-activated solution was combined with resin and the reaction was allowed to proceed at 22° C. DIC 1.07 eq was charged to the SPPS reaction, where the DMF/DCM ratio was about 1:1. The reaction was allowed to proceed at 22° C. A sample was tested for incomplete coupling using the Kaiser and/or TNBS color tests.

The material was washed followed by Fmoc deprotection and further washing. A sample was tested for residual Fmoc (UV test) and residual piperidine (pH). The Kaiser and/or TNBS color tests were conducted to ensure Fmoc deprotection had taken place.

DMF (0 L/kg); Acetic Anhydride (1.06 L/kg) and Pyridine (1.06 L/kg) were added to the solution and the solution was agitated for pre-activation. The pre-activation solution was combined with the resin and agitated at 22° C. The material was filtered and washed. A sample was tested for incomplete capping using the Kaiser and/or TNBS color tests. The material was slurry washed. The resin was dried under nitrogen without agitation. A sample of the dry resin was taken and tested for LOD and residual solvent. See FIG. 2.

Example 1B

Synthesis of the Main Chain Linear Fragment

Synthesis of the main chain linear fragment of AMG 416 is shown in FIG. 2. The peptide chain was built-up from the C-terminus to the N-terminus on Rink AM amide resin, 1 amino acid per cycle. Each cycle consists of 2 reaction steps: 1) Fmoc cleavage from the N-terminus; 2) Coupling of the next Fmoc-protected amino acid or final acetylation.

Start of SPPS: Rink AM amide resin (1.0 mole) was transferred into a SPPS reactor and washed with N,N'-Dimethylformamide (DMF).

Fmoc cleavage: The resin from the previous step was suspended in a solution of 20% piperidine in DMF for at least 10 min. Completion of Fmoc cleavage was monitored by ultraviolet (UV) absorption measurements. After completion of Fmoc cleavage, the resin was washed alternately with DMF and isopropanol (IPA) until a neutral pH was achieved.

Fmoc-amino acids coupling: Following the Fmoc cleavage step, coupling reaction was performed by mixing the resin with the solution of Fmoc-protected amino acid derivative (>1.2 mole) and activating reagents (>1.8 moles) (N,N'-diisopropylcarbodiimide (DIC) and ethyl (hydroxyimino)-cyanoacetate (Oxyma)) in DMF. For coupling of Fmoc-D-Cys(Trt)-OH, DIC and 1-hydroxybenzotriazole hydrate (HOBt) were used as activating agents, and a mixture of DMF and dichloromethane (DCM) was employed as the reaction solvent. The reaction mixture was stirred at ambient temperature overnight. Kaiser and TNBS tests were performed to monitor the completion of the coupling. Negative results from both Kaiser and TNBS tests were required before the process was moved on to the next cycle. After each coupling or capping step, the resin was alternately washed with DMF and IPA.

Final acetylation: After the final Fmoc-deprotection, the N-terminal amino group of the peptide was acetylated using acetic anhydride and pyridine in DMF. Kaiser and TNBS tests were performed to check the completion of the acetylation. If the acetylation was incomplete, the same acetylation procedure was then repeated until negative results from both Kaiser and TNBS tests were obtained.

Finally, the protected peptide backbone of the drug substance on the resin (AMG 416-Resin) was isolated by filtration, washed with DMF, IPA and acetonitrile (ACN) and dried under reduced pressure.

Example 2A

Cleavage of Main Chain Linear Fragment from Resin

A cocktail solution was prepared by combining DIW (0.16 L/kg); TFA (5.64 L/kg); TIPS (0.46 eq), and DPDS, (6.41 eq) at room temperature and then cooling the solution to 0±2° C. The peptide on the resin was added to the cocktail solution at 0±2° C. and the solution was heated to 25° C. and the reaction was allowed to proceed. The resin was removed by filtration and washed. The solution was held at −10° C. and a 6.8:1 solution of IPE:MeCN (24.5 L/kg) at −10° C. was added over time to control the temperature and precipitation. The reaction was allowed to proceed and the AMG 416 SPy intermediate product was filtered at −5° C. and washed. The SPy intermediate product was dried at 20° C. under full vacuum. See FIG. 3.

Example 2B

Cleavage of Main Chain Linear Fragment from Resin

The cleavage solution was prepared in a reactor by mixing TFA, H$_2$O, and triisopropylsilane (TIPS) in an approximate ratio of 96.9:2.6:0.5 (v/v/v). To the cleavage solution, DPDS (>1.2 moles) was added as the activating reagent of the sulfhydryl group of D-cysteine. AMG 416-Resin (1.0 mole) was charged to the reactor and the reaction mixture was stirred for >1 h at room temperature. The resin was filtered off. The filtrate and washing solutions were transferred into another reactor and cooled. A cold anti-solvent mixture of diisopropyl ether (IPE) and ACN was then charged to the solution to precipitate AMG 416-SPy. The suspension was filtered through a filter-drier and the filter cake of AMG 416-SPy was subsequently washed with ACN and IPE and dried at approximately 20° C. under reduced pressure on the filter drier.

Example 3

In-Situ Conjugation to L-Cys/Preparative HPLC

The AMG 416 SPy intermediate (1.0 mole) was added to a 0.2% TFA solution. L-Cysteine (>1.1 moles) was added to the solution and the reaction was allowed to proceed at room temperature for at least 15 min.

The purification of the crude AMG 416 was carried out by preparative chromatography using a C18 silica gel stationary phase using ACN/H$_2$O as the mobile phase and TFA as the modifier. The crude AMG 416 solution from Stage III was loaded on the column and a linear gradient method was used for the purification step. Elution was monitored by UV absorbance at 230 nm. After each loading, the column was flushed with 80% ACN in water (v/v) until a stable UV baseline was achieved. The fractions were stored at 5° C., they were sampled and then fractions having a desired purity (determined by HPLC) were pooled. The combined pools from the purification run were concentrated by performing the concentration run using the same HPLC column. The fractions were stored at 5° C. The fractions with desired purity (determined by HPLC) were lyophilized to isolate the AMG 416 TFA salt. See FIG. 4.

Example 4

Salt Conversion

The AMG 416 TFA salt was added to a solution of 15% water in IPA (v/v) 10 L/kg at 10° C. until full dissolution was observed. The solution was added to a solution of 12M aqueous HCl, 0.27 L/kg and IPA 49.4 L/kg over 3 hours via subsurface addition, resulting in direct precipitation of the AMG 416 4.5 HCl salt. The batch was aged for 3 hours and sampled for analysis.

The material was filtered and slurry washed with 96 wt % IPA, 10 L/kg. The cake was then re-slurried for 4 hours in 10 L/kg of 96% wt % IPA. The material was filtered and further slurry washed with 96% IPA, 10 L/kg and then IPA 10 L/kg. The material was dried under full vacuum at 25° C. The dry cake was dissolved in water 8 L/kg and the batch is concentrated via distillation to remove residual IPA and achieve the desired concentration. The solution temperature was kept below 25° C. throughout the distillation. See FIG. 5.

Example 5

Purification of the SPy Intermediate and Production of AMG 416 HCl

An alternative method for preparation of AMG 416 HCl salt is described here. As described in Example 2 above, the SPy intermediate product was dried at 20° C. under full vacuum after cleavage from the resin, precipitation and filtration. The precipitate was then dissolved in a 0.1% TFA aqueous solution and loaded onto a C-18 column for HPLC purification. The column was run at <60 bar and the solution temperature was 15-25° C. throughout. The eluents were 0.1% TFA in acetonitrile and 0.1% TFA in water. The fractions were stored at 5° C., they were sampled and then fractions were pooled. The combined pools from two runs were diluted and a concentration/purification run was performed using the same HPLC column to decrease the total volume and remove additional impurities. The fractions were stored at 5° C.

The fractions containing the AMG 416 SPy intermediate were subjected to azeotropic distillation to change the solvent from the 0.1% TFA to a 15% water in IPA solution, charging with IPA as needed. To the resultant AMG 416 SPy intermediate in IPA solution was then added L-Cysteine 1.15 eq and the reaction was allowed to proceed at room temperature for conjugation to occur and to form the AMG 416 TFA salt as described above in Example 4. The AMG 416 TFA solution was added to a solution of 12M aqueous HCl, 0.27 L/kg and IPA 49.4 L/kg over 3 hours via subsurface addition, resulting in direct precipitation of the AMG 416 4.5 HCl salt. The batch was aged for 3 hours and sampled for analysis.

The material was filtered and slurry washed with 96 wt % IPA, 10 L/kg. The cake was then re-slurried for 4 hours in 10 L/kg of 96% wt % IPA. The material was filtered and further slurry washed with 96% IPA, 10 L/kg and then IPA 10 L/kg. The material was dried under full vacuum at 25° C. The dry cake was dissolved in water 8 L/kg and the batch was concentrated via distillation to remove residual IPA and achieve the desired concentration. The solution temperature was kept below 25° C. throughout the distillation.

Example 6

Synthesis of H-D-Arg(Pbf)-OH

Synthesis of the main chain linear fragment as described in Example 1 requires the use of Fmoc-D-Arg(Pbf)-OH for addition of the D-arginine subunits, which make up 4 of the 7 residues in the linear fragment. An improved and more efficient method for synthesizing Fmoc-D-Arg(Pbf)-OH is described below.

The synthesis starts with the protection of the amino group of D-Arg by Di-tert-butyl dicarbonate (Boc$_2$O), yielding Boc-D-Arg-OH in approximately quantitative yield after isolation by crystallization under the standard procedure reported in the literature. The arginine side chain guanidine group was protected with a Pbf group by a one-hour addition (0-5° C.) of a 10/1 acetone/THF solution of Pbf-Cl (1.3 eq) in the presence of aqueous NaOH (4.3 eq)/NaI (5% mol) as the base, producing Boc-D-Arg(Pbf)-OH (85-90% assay yield) See FIG. 6. The Boc-D-Arg(Pbf)-OH in IPAc solution was treated with 4.8 eq of concentrated HCl at 20° C. for approximately 6 h. After the reaction, the organic layer was discarded and the crude product was isolated from the aqueous layer by adjusting the pH to 5 using NaOH, after which a white suspension was observed. See FIG. 7. When the supernatant had a concentration of approximately 3 mg/mL at 20° C., the supernatant was filtered at room temperature, and the resultant cake washed with water and dried under a vacuum. The overall assay yield after this step was about 80-85%. The purity of H-D-Arg(Pbf)-OH was increased to >98.5% by a first re-crystallization from 3/1 water/IPA (v/v). When the supernatant had a concentration of about 7 mg/mL it was filtered and dried under vacuum. After this step, the overall assay yield was about 75%. (Typically about 10% of the product loss is observed in this step). A second re-crystallization step from 4/1 water/IPA (v/v) was performed. Filtering was done when the supernatant concentration was about 3.7 mg/mL. The second re-crystallization increased the purity of H-D-Arg(Pbf)-OH to about 99.84 area percentage purity (LCAP) by HPLC with no impurities more than 0.2 LCAP. The typical yield of this step is about 93% with about 5% product loss. The H-D-Arg(Pbf)-OH was then reacted with FmocOSu according to standard protocols and the product Fmoc-D-Arg(Pbf)-OH was isolated using the standard procedure in the literature.

What is claimed is:

1. A method for preparing etelcalcetide, as set forth in formula (1):

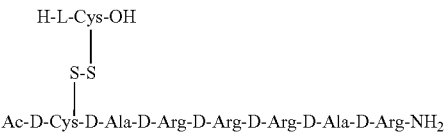

or a pharmaceutically acceptable salt thereof, the method comprising:
contacting a peptide having the structure of Ac-D-Cys(SPy)-D-Ala-D-Arg-D-Arg-D-Arg-D-Ala-D-Arg-NH2 (SEQ ID NO:4) with L-Cys to produce a conjugated product of formula (1).

2. The method of claim 1, wherein said contacting comprises dissolving the peptide in an aqueous solution comprising L-Cys and trifluoroacetic acid (TFA).

3. The method of claim 2, wherein said contacting occurs at room temperature for about 15 minutes.

4. The method of claim 1, further comprising lyophilizing the conjugated product.

5. The method of claim 4, further comprising contacting the conjugated product with an aqueous solution comprising isopropyl alcohol and hydrochloride (HCl), thereby producing a precipitate comprising etelcalcetide HCl (SEQ ID NO:1).

6. The method of claim 5, further comprising washing the precipitate comprising etelcalcetide HCl (SEQ ID NO:1) with isopropyl alcohol.

7. The method of claim 6, further comprising dissolving the isopropyl alcohol washed precipitate in water to produce a dissolved precipitate.

8. The method of claim 7, further comprising concentrating the dissolved precipitate via distillation.

9. The method of claim 5, further comprising purifying the precipitate by HPLC.

10. The method of claim 1, wherein the conjugated product is represented by a formula Ac-D-Cys(L-Cys-OH)-D-Ala-D-Arg-D-Arg-D-Arg-D-Ala-D-Arg-NH₂ (SEQ ID NO: 1) or a pharmaceutically acceptable salt thereof.

11. The method of claim 10, further comprising contacting the conjugated product with an aqueous solution comprising isopropyl alcohol (IPA) and HCl, thereby producing a precipitate comprising a HCl salt of SEC ID NO: 1.

12. The method of claim 4, wherein the method further comprises deriving the peptide having structure Ac-D-Cys(SPy)-D-Ala-D-Arg-D-Arg-D-Arg-D-Ala-D-Arg-NH₂ (SEQ ID NO:4) from a resin-bound peptide having a structure of Ac-D-Cys(Trt)-D-Ala-D-Arg(Pbf)-D-Arg(Pbf)-D-Arg(Pbf)-D-Ala-D-Arg(Pbf)-[Resin] (SEQ ID NO:3).

13. The method of claim 12, wherein the deriving comprises contacting the resin-bound peptide with a solution comprising water, trifluoroacetic acid, triisopropylsilane and dipyridyldisulfide.

14. The method of claim 1, wherein the peptide comprises a TFA salt of Ac-D-Cys(SPy)-D-Ala-D-Arg-D-Arg-D-Arg-D-Ala-D-Arg-NH₂ (SEQ ID NO:4).

* * * * *

```
                           SEQUENCE LISTING

<160> NUMBER OF SEQ ID NOS: 4

<210> SEQ ID NO 1
    <211> LENGTH: 7
    <212> TYPE: PRT
    <213> ORGANISM: Artificial Sequence
    <220> FEATURE:
    <223> OTHER INFORMATION: Synthetic peptide
    <220> FEATURE:
    <221> NAME/KEY: VARIANT
    <222> LOCATION: (1)..(1)
    <223> OTHER INFORMATION: Xaa = D-Cys
    <220> FEATURE:
    <221> NAME/KEY: MOD_RES
    <222> LOCATION: (1)..(1)
    <223> OTHER INFORMATION: N-terminal acetylation
    <220> FEATURE:
    <221> NAME/KEY: DISULFID
    <222> LOCATION: (1)..(1)
    <223> OTHER INFORMATION: Cys-Cys disulfide bond to Cys
    <220> FEATURE:
    <221> NAME/KEY: VARIANT
    <222> LOCATION: (2), (6)
    <223> OTHER INFORMATION: Xaa = D-Ala
    <220> FEATURE:
    <221> NAME/KEY: VARIANT
    <222> LOCATION: (3), (4), (5), (7)
    <223> OTHER INFORMATION: Xaa = D-Arg
    <220> FEATURE:
    <221> NAME/KEY: MOD_RES
    <222> LOCATION: (7)
    <223> OTHER INFORMATION: C-terminal amidation

<400> SEQUENCE: 1

Xaa Xaa Xaa Xaa Xaa Xaa Xaa
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: Synthetic peptide
    <220> FEATURE:
    <221> NAME/KEY: VARIANT
    <222> LOCATION: (1)..(1)
    <223> OTHER INFORMATION: Xaa = D-Cys(trt)
    <220> FEATURE:
    <221> NAME/KEY: MOD_RES
    <222> LOCATION: (1)..(1)
    <223> OTHER INFORMATION: attached to Fmoc
    <220> FEATURE:
    <221> NAME/KEY: VARIANT
    <222> LOCATION: (2), (6)
    <223> OTHER INFORMATION: Xaa = D-Ala
    <220> FEATURE:
    <221> NAME/KEY: VARIANT
    <222> LOCATION: (3), (4), (5), (7)
    <223> OTHER INFORMATION: Xaa = D-Arg(Pfb)
    <220> FEATURE:
    <221> NAME/KEY: MOD_RES
    <222> LOCATION: (7)
    <223> OTHER INFORMATION: attached to resin

<400> SEQUENCE: 2
```

Xaa Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys(Trt)
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg(Pbf)
<220> FEATURE:
<221> NAME/KEY: MOD_RES
<222> LOCATION: (7)
<223> OTHER INFORMATION: attached to resin

<400> SEQUENCE: 3

Xaa Xaa Xaa Xaa Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys(SPy)
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 4

Xaa Xaa Xaa Xaa Xaa Xaa Xaa
1               5